United States Patent
Ding et al.

(10) Patent No.: US 12,131,474 B2
(45) Date of Patent: Oct. 29, 2024

(54) THREE-WAY U-NET METHOD FOR ACCURATELY SEGMENTING UNCERTAIN BOUNDARY OF RETINAL BLOOD VESSEL

(71) Applicant: NANTONG UNIVERSITY, Jiangsu (CN)

(72) Inventors: Weiping Ding, Jiangsu (CN); Ying Sun, Jiangsu (CN); Tao Hou, Jiangsu (CN); Xinjie Shen, Jiangsu (CN); Hengrong Ju, Jiangsu (CN); Jiashuang Huang, Jiangsu (CN); Haipeng Wang, Jiangsu (CN); Tingzhen Qin, Jiangsu (CN); Yu Geng, Jiangsu (CN); Ming Li, Jiangsu (CN); Haowen Xue, Jiangsu (CN); Zhongyi Wang, Jiangsu (CN)

(73) Assignee: NANTONG UNIVERSITY, Jiangsu (CN)

( * ) Notice: Subject to any disclaimer, the term of this patent is extended or adjusted under 35 U.S.C. 154(b) by 0 days.

(21) Appl. No.: 18/571,258

(22) PCT Filed: May 24, 2023

(86) PCT No.: PCT/CN2023/095984
§ 371 (c)(1),
(2) Date: Dec. 18, 2023

(87) PCT Pub. No.: WO2023/236773
PCT Pub. Date: Dec. 14, 2023

(65) Prior Publication Data
US 2024/0289952 A1 Aug. 29, 2024

(30) Foreign Application Priority Data
Jun. 6, 2022 (CN) .......................... 202210632508.8

(51) Int. Cl.
*G06T 7/00* (2017.01)
*G06T 5/30* (2006.01)
(Continued)

(52) U.S. Cl.
CPC .............. *G06T 7/0012* (2013.01); *G06T 7/12* (2017.01); *G16H 15/00* (2018.01); *G06T 5/30* (2013.01);
(Continued)

(58) Field of Classification Search
CPC ..................... G06T 7/0012; G06T 7/12; G06T 2207/10024; G06T 2207/20081;
(Continued)

(56) References Cited

U.S. PATENT DOCUMENTS

| 2007/0036434 | A1  | 2/2007 | Saveliev |
| 2021/0082184 | A1* | 3/2021 | Claessen ................ A61B 6/51 |
| 2023/0260119 | A1* | 8/2023 | Soeda ................ G06T 7/0012 382/128 |

FOREIGN PATENT DOCUMENTS

| CN | 111161287 | 5/2020 |
| CN | 113487618 | 10/2021 |

(Continued)

OTHER PUBLICATIONS

Zhang et al. "Blood Vessel Segmentation in Fundus Images Based on Improved Loss Function." Chines Automation Congress (CAC), Nov. 22, 2019, pp. 4017-4021 (Year: 2019).*
(Continued)

*Primary Examiner* — Jon Chang
(74) *Attorney, Agent, or Firm* — JCIPRNET

(57) ABSTRACT

The present disclosure is a three-way U-Net method for accurately segmenting an uncertain boundary of a retinal blood vessel, includes: describing an uncertainty of a blood vessel boundary label, constructing an upper bound and a
(Continued)

lower bound of the uncertain boundary based on the dilation operator and the erosion operator respectively to obtain a maximum value and a minimum value for the blood vessel boundary, and mapping the boundary with uncertain information into one range; combining an uncertainty representation of the boundary with a loss function, and designing a three-way loss function; training network parameters by adopting a stochastic gradient descent algorithm and utilizing a total loss of the three-way loss function; and designing and implements an auxiliary diagnosis application system for intelligently segmenting the retinal blood vessel with functions of the fundus data acquisition, the intelligent accurate segmentation and the auxiliary diagnosis for the retinal blood vessel.

2 Claims, 4 Drawing Sheets

(51) Int. Cl.
G06T 7/12 (2017.01)
G16H 15/00 (2018.01)
(52) U.S. Cl.
CPC .............. G06T 2207/10024 (2013.01); G06T 2207/20081 (2013.01); G06T 2207/20084 (2013.01); G06T 2207/30041 (2013.01)

(58) Field of Classification Search
CPC . G06T 2207/20084; G06T 2207/30041; G06T 5/30; G06T 2207/20021; G16H 15/00; G06N 3/045; G06N 3/08
See application file for complete search history.

(56) References Cited

FOREIGN PATENT DOCUMENTS

| CN | 113643303 | | 11/2021 |
| CN | 114066884 | A * | 2/2022 |
| CN | 114266888 | | 4/2022 |
| CN | 114283158 | A * | 4/2022 |
| CN | 114494196 | | 5/2022 |
| CN | 114972279 | | 8/2022 |
| WO | 2018125580 | | 7/2018 |

OTHER PUBLICATIONS

Burewar et al. "Diabetic Retinopathy Detection by Retinal segmentation with Region Merging Using CNN." IEEE 13th International Conference on Industrial and Information Systems (ICIIS), Dec. 1, 2018, pp. 136-142 (Year: 2018).*

"International Search Report (Form PCT/ISA/210) of PCT/CN2023/095984", mailed on Sep. 26, 2023, pp. 1-4.

* cited by examiner describing the uncertainty of the blood vessel boundary label by utilizing the dilation operator and the erosion operator of the mathematical morphology, constructing the upper bound and the lower bound of the uncertain boundary based on the dilation operator and the erosion operator respectively combing the uncertainty representation of the boundary with the loss function, and designing the three-way loss function training network parameters by adopting the stochastic gradient descent algorithm and utilizing the total loss of the three-way loss function designing and implementing the auxiliary diagnosis application system for intelligently segmenting the retinal blood vessel with functions of the fundus data acquisition, the intelligent accurate segmentation and the auxiliary diagnosis for the retinal blood vessel

FIG. 1

THREE-WAY U-NET METHOD FOR ACCURATELY SEGMENTING UNCERTAIN BOUNDARY OF RETINAL BLOOD VESSEL

CROSS-REFERENCE TO RELATED APPLICATION

This application is a 371 of international application of PCT application serial no. PCT/CN2023/095984, filed on May 24, 2023, which claims the priority benefit of China application serial no. 202210632508.8, filed on Jun. 6, 2022. The entirety of each of the above-mentioned patent applications is hereby incorporated by reference herein and made a part of this specification.

TECHNICAL FIELD

The present disclosure relates to the technical field of the medical information intelligent processing, in particular to a three-way U-Net method for accurately segmenting an uncertain boundary of a retinal blood vessel.

BACKGROUND

As an indispensable part of the national health, the eye health is a public health issue and a social issue involving people's well-being, which has attracted high attentions from the National Health Commission. The medical imaging technology is a method for diagnosing and monitoring various diseases of the human body, which can generate image representations on different parts of the human body. The fundus camera is a non-invasive and cost-effective way to acquire the fundus image, which enables the physician specialists to obtain the color fundus image in a non-invasive manner. Human red green blue (RGB) color fundus image is a projection on the inner surface of the eye which provides rich pathological information. At present, due to the relatively low contrast between the retinal blood vessel and the background in fundus images, the fine blood vessel structure, and the considerable heterogeneity in shape, color and texture, the problems such as time-consuming, complicated demarcation and strong subjectivity exist in the manual demarcating for the retinal blood vessel boundary in the fundus image, which causes certain differences among the gold standard maps demarcated by different experts. Manually segmented category labels fail to capture the uncertainty associating with the process that the experts assign the category labels.

In addition, although the demand for the ophthalmic service from China Grass-roots people is increasing, the number of ophthalmologists in China is limited, the distribution of the medical resources is uneven, and the excellent resources are concentrated in large cities and tertiary hospitals, while ophthalmic resources in remote districts and grassroots hospitals are relatively short, it is significant to establish an informationize eye health platform for solving this problem. Meanwhile, the establishment of an ophthalmology case database to accumulate a large amount of fundus image data can not only provide data support for the clinical scientific research, but also be used to train an intelligent and accurate segmentation model of the retinal blood vessel based on deep learning technology, which provides diagnostic basis for assisting doctors in diagnosing various ophthalmology diseases and cardiovascular and cerebrovascular diseases.

SUMMARY

The objectives of the present disclosure are to solve the above technical problems, and a three-way U-Net method for accurately segmenting an uncertain boundary of a retinal blood vessel is provided.

The technical solutions adopted in the present disclosure are as follows. Provided is a three-way U-Net method for accurately segmenting an uncertain boundary of a retinal blood vessel, and the method comprises the following steps.

In S1, a feature extraction module for extracting retinal vessel features layer by layer is constructed in a feature encoding part of a U-net. The feature extraction module includes two 3×3 convolutional layers, one Dropout layer, one Relu excitation layer, and one 2×2 maximum pooling layer. A recovery feature module for recovering a size of an image and restore position information on the image is constructed in a feature decoding part of a U-net module. The recovery feature module includes one 2×2 upsampling layer and two 3×3 convolutional layers. Symmetrical layers of an upsampling and a sub-sampling are connected by a skip connection. A higher layer feature map is spliced with a bottom layer feature map to serve as an input for a subsequent layer, so that the model can fuse the higher and lower layer features to learn more blood vessel features to obtain a more accurate output feature map. After a feature size of the image is recovered, two 1×1 convolutional kernels are convolved to obtain a feature map with a channel number of 2, one channel represents a vascular category, and another channel represents a non-vascular category, and a probability that each pixel point in the image belongs to each category is calculated by a softmax layer.

In S2, an uncertainty of a retinal blood vessel boundary label is described by utilizing a dilation operator and an erosion operator of a mathematical morphology. An upper bound map $I_{dilate}$ of an uncertain boundary of the retinal blood vessel is constructed based on the dilation operator, a lower bound map $I_{erose}$ of the uncertain boundary of the retinal blood vessel is constructed based on the erosion operator, respectively, to obtain a maximum value and a minimum value for a blood vessel boundary, and the boundary with uncertain information is mapped into one range.

In S3, the uncertainty of the boundary is combined with a loss function and a three-way loss function are proposed. A cross entropy loss between a retinal blood vessel prediction boundary map $I_{predict}$ and a retinal blood vessel manual segmentation gold standard map $I_{true}$, a cross entropy loss between the upper bound map $I_{dilate}$ of the uncertain boundary of the retinal blood vessel and the lower bound map $I_{erose}$ of the uncertain boundary of the retinal blood vessel are calculated by the loss function. An eventual loss is generated by a weighted fusion, and a formula for calculating the eventual loss is as follows:

$$\text{Loss} = l_1 + \alpha \times l_2 + (1 - \alpha) \times l_3 \quad (1)$$

wherein $l_1$ denotes the cross entropy loss between the retinal blood vessel prediction image $I_{predict}$ and the retinal blood vessel manual segmentation gold standard map $I_{true}$, and $l_1$ is calculated as shown in Formula (2); $l_2$ denotes a cross entropy loss between the retinal blood vessel prediction image $I_{predict}$ and the lower bound map $I_{dilate}$ of the uncertain boundary of the retinal blood vessel constructed based on the erosion operator, and $l_2$ is calculated as shown in Formula (3); $l_3$ denotes a cross entropy loss between the retinal blood vessel prediction image $I_{predict}$ and the upper bound map $I_{erose}$ of the uncertain boundary of the retinal blood vessel constructed based on the dilation operator, and $l_2$ is calculated as shown in Formula (4); α and 1−α are hyper-parameters, a denotes a loss weight between the retinal blood vessel prediction image $I_{predict}$ and the lower bound map $I_{erose}$ of the uncertain boundary of the retinal blood vessel, and 1−α denotes a loss weight between the retinal blood vessel prediction image $I_{predict}$ and the upper bound map $I_{dilate}$ of the uncertain boundary of the retinal blood vessel;

$$l_1 = -\sum_{i=1}^{n} I_{true} \log(I_{predict}) \qquad (2)$$

$$l_2 = -\sum_{i=1}^{n} I_{erose} \log(I_{predict}) \qquad (3)$$

$$l_3 = -\sum_{i=1}^{n} I_{dilate} \log(I_{predict}) \qquad (4)$$

wherein n denotes a number of categories contained in the images; and network parameters are trained by adopting a stochastic gradient descent algorithm by utilizing a total loss of the three-way loss function.

In S4, an auxiliary diagnosis application system for intelligently segmenting the retinal blood vessel is implemented by utilizing a Django framework in Python. The application system includes a fundus data acquisition, an intelligent accurate segmentation for a retinal blood vessel and an auxiliary diagnosis for the retinal blood vessel. The fundus data is responsible for collecting basic information on a patient as well as left and right eye images of the patient captured by medical equipment. The intelligent accurate segmentation for the retinal blood vessel is to segment the blood vessel in the captured left and right eye images of the patient by utilizing a U-Net model based on the three-way loss function (TWD-UNet), and segmentation results are uploaded to a remote diagnostic module. The auxiliary diagnosis is mainly that the doctor analyze a patient's condition and provides diagnostic advice according to the basic information on the patient, color left and right eye images captured by a fundus camera and a corresponding segmented image of the retinal blood vessel to generate a downloadable and printable electronic diagnosis report.

Further, as a preferred embodiment in the present disclosure, specific steps for the step S2 are as follows.

In S2.1, a M×M×3 retinal blood vessel image I is eroded by Formula (5) to eliminate tiny targets in the retinal blood vessel image, Formula (5) is as follows:

$$I ! D = \{x, y \mid (D)_{xy} \subseteq I\} \qquad (5)$$

wherein $$D = \begin{bmatrix} 1 & 1 & 1 \\ 1 & 1 & 1 \\ 1 & 1 & 1 \end{bmatrix}$$

denotes a structure element, a center is taken as an anchor point in the structure element D, the structure element D is slid on the retinal blood vessel image/with the anchor point O as the center, an entire image is traversed, a value for a pixel point at a position in the image where the anchor point is passed is set as a minimum value for a pixel point in the image corresponding to the structure element.

In S2.2, the M×M×3 retinal blood vessel image I is dilated by utilizing Formula (6) to enlarge an area of a target region.

In S2.3, the target regions are fused by the dilation of the image to infill small particle noises in the target regions, since a distance between the target regions is relatively close, a formula for the dilation is as follows:

$$I \oplus E = \{x, y \mid (E)_{xy} \cap I \neq \emptyset\} \qquad (6)$$

wherein $$E = \begin{bmatrix} 1 & 1 & 1 \\ 1 & 1 & 1 \\ 1 & 1 & 1 \end{bmatrix}$$

denotes a structure element, a center is taken as an anchor point in the structure element E, the structure element E is slid on the retinal blood vessel image I with the anchor point O as the center, the entire image is traversed to determine whether an intersection of pixel values in the structure element region and in the corresponding image area is empty, if the intersection is an empty set, an image position corresponding to the anchor point of the structure element is set to 0, else, the image position corresponding to the anchor point of the structure element is set to 1.

Compared with the prior art, the three-way U-Net method for accurately segmenting the uncertain boundary of the retinal blood vessel in the present disclosure has the following technical effects by adopting the above technical solutions.

The present disclosure can significant improve the accuracy on the segmentation of the uncertain boundary of the retinal blood vessel, provides cheap and convenient profession diagnosis suggestion for grassroots hospitals and third-level first class hospitals, and provides personalized medical services for patients.

BRIEF DESCRIPTION OF THE DRAWINGS

FIG. 1 illustrates a schematic diagram of a three-way U-Net method for accurately segmenting of an uncertain boundary of a retinal blood vessel in the present disclosure.

DETAILED DESCRIPTION OF THE EMBODIMENTS

The present disclosure will be further described below with reference to the accompanying drawings and the embodiments.

Figure 2:
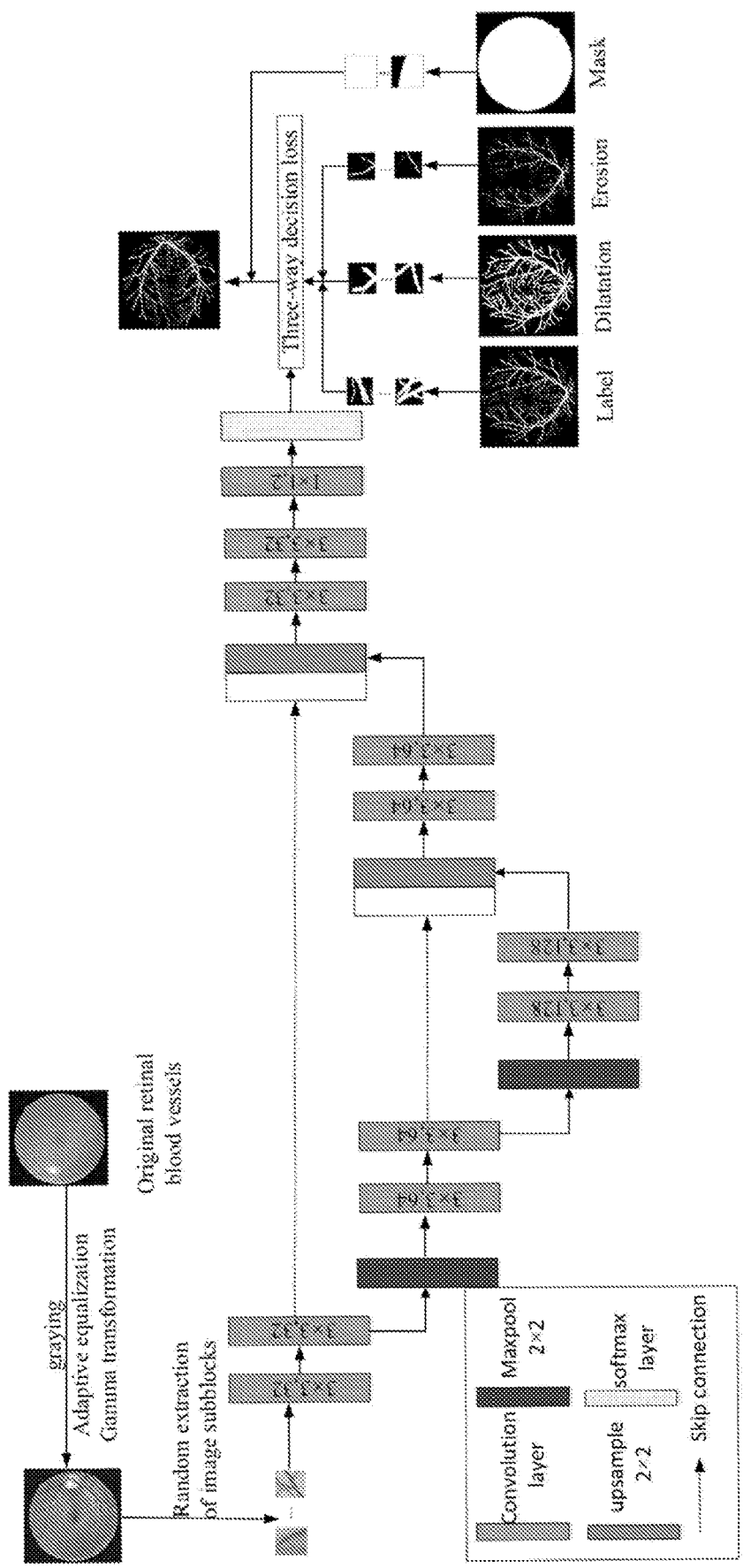
FIG. 2 illustrates a schematic diagram of a U-Net model based on a three-way loss function in the present disclosure.

As illustrated in FIGS. 1 to 2, provided is a three-way U-Net method for accurately segmenting an uncertain boundary of a retinal blood vessel, and the method comprises the following steps.

In S1, a feature extraction module for extracting retinal vessel features layer by layer is constructed in a feature encoding part of a U-net. The feature extraction module includes two 3×3 convolutional layers, one Dropout layer, one Relu excitation layer, and one 2×2 maximum pooling layer. A recovery feature module for recovering a size of an image and restore position information on the image is constructed in a feature decoding part of a U-net module. The recovery feature module includes one 2×2 upsampling layer and two 3×3 convolutional layers. Symmetrical layers of an upsampling and a sub-sampling are connected by a skip connection. A higher layer feature map is spliced with a bottom layer feature map to serve as an input for a subsequent layer, so that the model can fuse the higher and lower layer features to learn more blood vessel features to obtain a more accurate output feature map. After a feature size of the image is recovered, two 1×1 convolutional kernels are convolved to obtain a feature map with a channel number of 2, one channel represents a vascular category, and another channel represents a non-vascular category, and a probability that each pixel point in the image belongs to each category is calculated by a softmax layer.

In S2, an uncertainty of a retinal blood vessel boundary label is described by utilizing a dilation operator and an erosion operator of a mathematical morphology. An upper bound map $I_{dilate}$ of an uncertain boundary of the retinal blood vessel is constructed based on the dilation operator, a lower bound map $I_{erose}$ of the uncertain boundary of the retinal blood vessel is constructed based on the erosion operator, respectively, to obtain a maximum value and a minimum value for a blood vessel boundary, and the boundary with uncertain information is mapped into one range.

Figure 3:
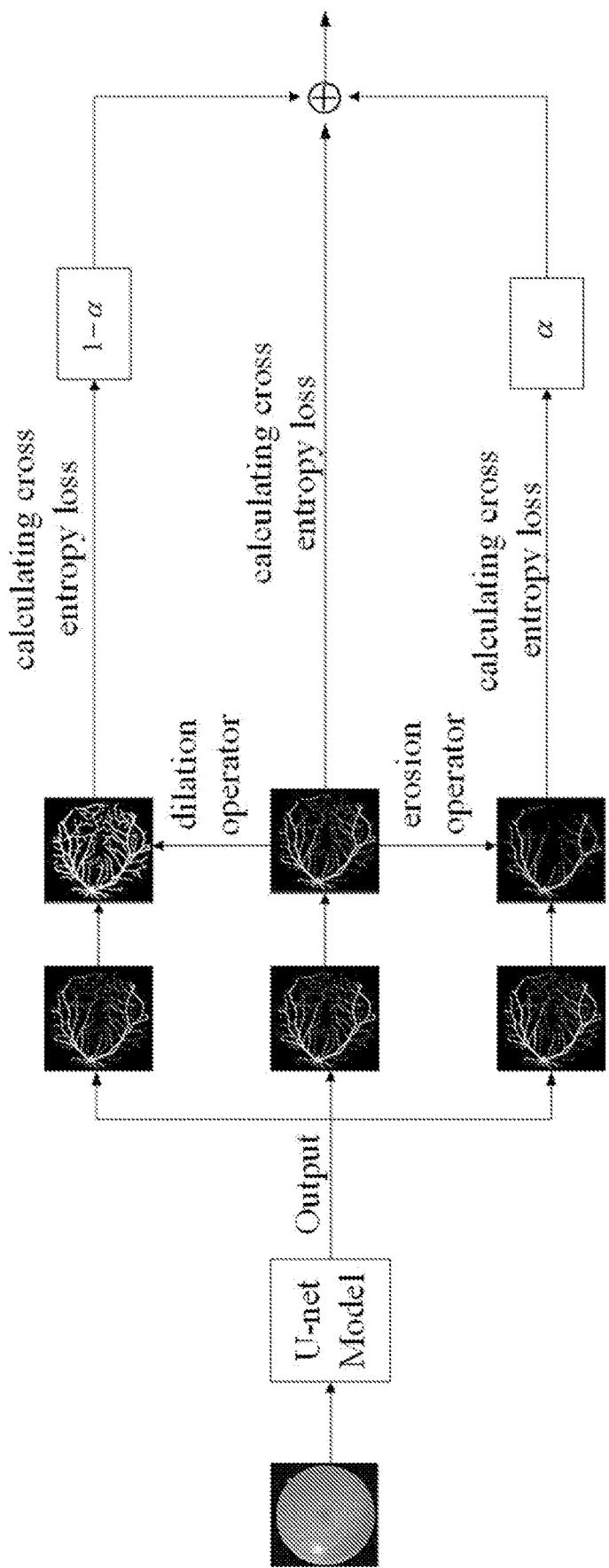
FIG. 3 illustrates a structure diagram of the three-way loss function in the present disclosure.

As illustrated in FIG. 3, in S3, the uncertainty of the boundary is combined with a loss function and a three-way loss function are proposed. A cross entropy loss between a retinal blood vessel prediction boundary map $I_{predict}$ and a retinal blood vessel manual segmentation gold standard map $I_{true}$, a cross entropy loss between the upper bound map $I_{dilate}$ of the uncertain boundary of the retinal blood vessel and the lower bound map $I_{erose}$ of the uncertain boundary of the retinal blood vessel are calculated by the loss function. An eventual loss is generated by a weighted fusion, and a formula for calculating the eventual loss is as follows:

$$\text{Loss} = l_1 + \alpha \times l_2 + (1-\alpha) \times l_3 \qquad (1)$$

wherein $l_1$ denotes the cross entropy loss between the retinal blood vessel prediction image $I_{predict}$ and the retinal blood vessel manual segmentation gold standard map $I_{true}$, and $l_1$ is calculated as shown in Formula (2); $l_2$ denotes a cross entropy loss between the retinal blood vessel prediction image $I_{predict}$ and the lower bound map $I_{dilate}$ of the uncertain boundary of the retinal blood vessel constructed based on the erosion operator, and $l_2$ is calculated as shown in Formula (3); $l_3$ denotes a cross entropy loss between the retinal blood vessel prediction image $I_{predict}$ and the upper bound map $I_{erose}$ of the uncertain boundary of the retinal blood vessel constructed based on the dilation operator, and $l_3$ is calculated as shown in Formula (4); $\alpha$ and $1-\alpha$ are hyper-parameters, $\alpha$ denotes a loss weight between the retinal blood vessel prediction image $I_{predict}$ and the lower bound map $I_{erose}$ of the uncertain boundary of the retinal blood vessel, and $1-\alpha$ denotes a loss weight between the retinal blood vessel prediction image $I_{predict}$ and the upper bound map $I_{dilate}$ of the uncertain boundary of the retinal blood vessel;

$$l_1 = -\sum_{i=1}^{n} I_{true} \log(I_{predict}) \qquad (2)$$

$$l_2 = -\sum_{i=1}^{n} I_{erose} \log(I_{predict}) \qquad (3)$$

$$l_3 = -\sum_{i=1}^{n} I_{dilate} \log(I_{predict}) \qquad (4)$$

wherein n denotes a number of categories contained in the images; and network parameters are trained by a stochastic gradient descent algorithm by utilizing a total loss of the three-way loss function.

DESCRIPTION

Figure 4:
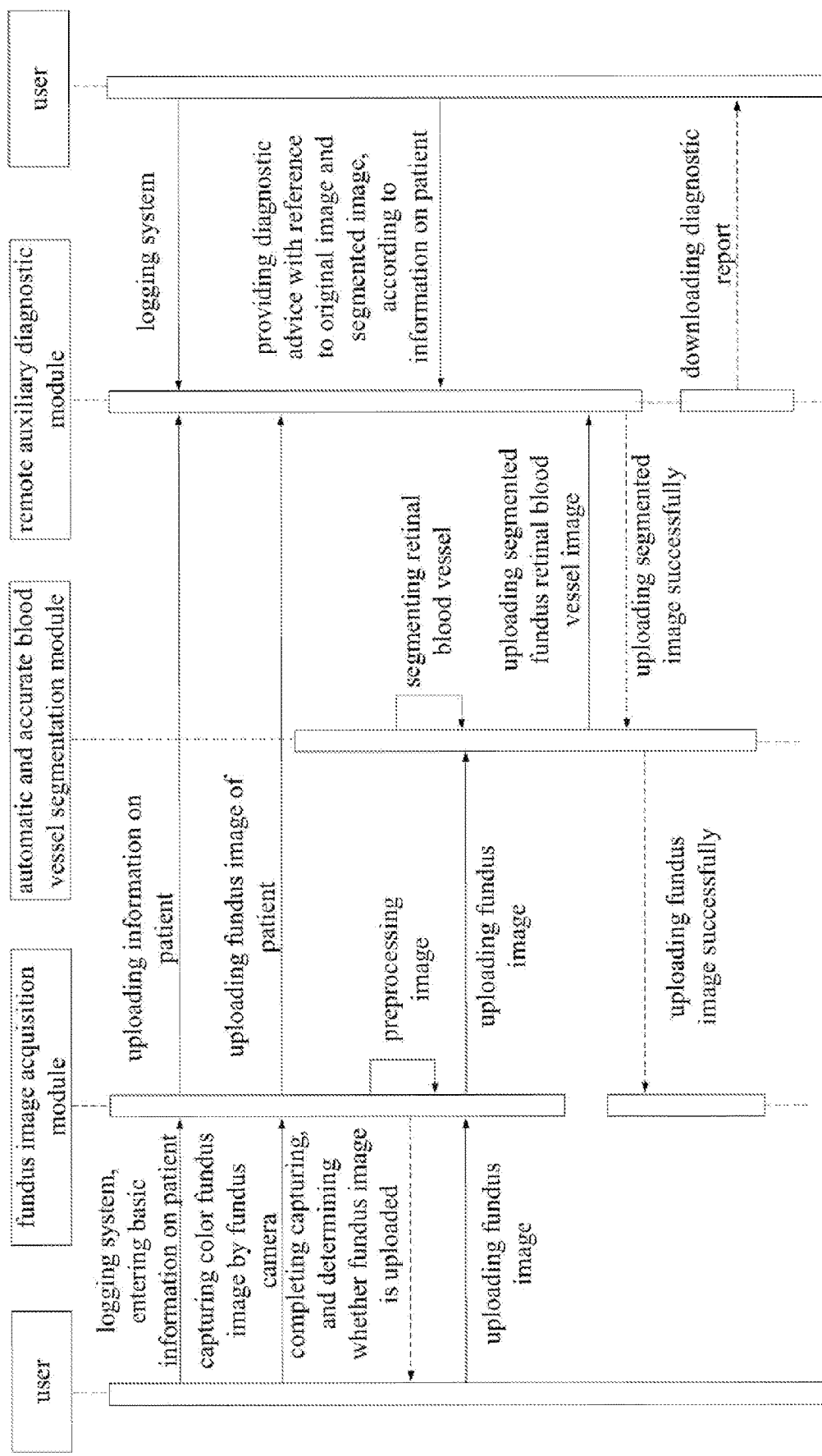
FIG. 4 illustrates a timing diagram of the three-way U-Net method for accurately segmenting the uncertain boundary of the retinal blood vessel and the auxiliary diagnostic application system in the present disclosure.

As illustrated in FIG. 4, in S4, an auxiliary diagnosis application system for intelligently segmenting the retinal blood vessel is implemented by utilizing a Django framework in Python. The application system includes a fundus data acquisition, an intelligent accurate segmentation for a retinal blood vessel and an auxiliary diagnosis for the retinal blood vessel. The fundus data is responsible for collecting basic information on a patient as well as left and right eye images of the patient captured by medical equipment. The intelligent accurate segmentation for the retinal blood vessel is to segment the blood vessel in the captured left and right eye images for the patient by utilizing a U-Net model based on the three-way loss function (TWD-UNet), and segmentation results are uploaded to a remote diagnostic module. The auxiliary diagnosis is mainly that the doctor analyze a patient's condition and provides diagnostic advice according to the basic information on the patient, color left and right eye images captured by a fundus camera and a corresponding segmented image of the retinal blood vessel to generate a downloadable and printable electronic diagnosis report.

The specific steps for step S2 are as follows.

In S2.1, a M×M×3 retinal blood vessel image I is eroded by Formula (5) to eliminate tiny targets in the retinal blood vessel image, Formula (5) is as follows:

$$I \mathbin{!} D = \{x, y \mid (D)_{xy} \subseteq I\} \qquad (5)$$

wherein $$D = \begin{bmatrix} 1 & 1 & 1 \\ 1 & 1 & 1 \\ 1 & 1 & 1 \end{bmatrix}$$

denotes a structure element, a center is taken as an anchor point wherein in the structure element D, the structure element D is slid on the retinal blood vessel image I with the anchor point O as the center, an entire image is traversed, a value for a pixel point at a position in the image where the anchor point is passed is set as a minimum value for a pixel point in the image corresponding to the structure element.

In S2.2, the M×M×3 retinal blood vessel image I is dilated by utilizing Formula (6) to enlarge an area of a target region.

In S2.3, the target regions are fused by the dilation of the image to infill small particle noises in the target regions, since a distance between the target regions is relatively close, a formula for the dilation is as follows:

$$I \oplus E = \{x, y \mid (E)_{xy} \cap I \neq \emptyset\} \quad (6)$$

wherein $$E = \begin{bmatrix} 1 & 1 & 1 \\ 1 & 1 & 1 \\ 1 & 1 & 1 \end{bmatrix}$$

denotes a structure element, a center is taken as an anchor point in the structure element E, the structure element E is slid on the retinal blood vessel image/with the anchor point O as the center, the entire image is traversed to determine whether an intersection of pixel values in the structure element region and in the corresponding image area is empty, if the intersection is an empty set, an image position corresponding to the anchor point of the structure element is set to 0, else, the image position corresponding to the anchor point of the structure element is set to 1.

The present disclosure describes the uncertainty of the blood vessel boundary label by utilizing the dilation operator and the erosion operator of the mathematical morphology, constructs the upper boundary and the lower boundary of the uncertain boundary based on the dilation operator and the erosion operator to obtain the maximum value and the minimum value for the blood vessel boundary, and maps the boundary with the uncertain information into one range, combines the uncertain representation of the boundary with the loss function and designs a three-way loss function, trains network parameters by adopting the stochastic gradient descent algorithm by utilizing the total loss of the three-way loss function, to design and implement the auxiliary diagnosis application system for intelligently segmenting the retinal blood vessel with the functions of the fundus data acquisition, the intelligent accurate segmentation and the auxiliary diagnosis for the retinal blood vessel.

The objectives, technical solutions and the beneficial effects of the present disclosure are further described in details by the above specific embodiments. It should be understood that the above-mentioned specific embodiments are merely specific embodiments of the present disclosure, and are not intended to limit the present disclosure. Without departing from the concept and the principle of the present disclosure any equivalent changes and modifications made by those people skilled in the art should belong to the protection scope of the present disclosure.

What is claimed is:

1. A three-way U-Net method for accurately segmenting an uncertain boundary of a retinal blood vessel, comprising the following steps:
    S1, constructing, in a feature encoding part of a U-net, a feature extraction module for extracting retinal vessel features layer by layer, wherein the feature extraction module includes two 3×3 convolutional layers, one Dropout layer, one Relu excitation layer, and one 2×2 maximum pooling layer; constructing, in a feature decoding part of a U-net module, a recovery feature module for recovering a size of an image and restore position information on the image, wherein the recovery feature module includes one 2×2 upsampling layer and two 3×3 convolutional layers; connecting symmetrical layers of an upsampling and a sub-sampling by a skip connection; splicing a higher layer feature map with a bottom layer feature map to serve as an input for a subsequent layer to enable the model to fuse higher features with lower features to learn more blood vessel features and obtain a more accurate output feature map; and convolving, after recovering a feature size of the image, two 1×1 convolutional kernels to obtain a feature map with a channel number of 2, wherein one channel represents a vascular category, and another channel represents a non-vascular category; and calculating, by a softmax layer, a probability that each pixel point in the image belongs to each category;
    S2, describing, based on a dilation operator and an erosion operator of a mathematical morphology, an uncertainty of a retinal blood vessel boundary label; constructing, based on the dilation operator, an upper bound map $I_{dilate}$ of an uncertain boundary of the retinal blood vessel, and constructing, based on the erosion operator, a lower bound map $I_{erose}$ of the uncertain boundary of the retinal blood vessel respectively, to obtain a maximum value and a minimum value for a blood vessel boundary; and mapping a boundary with uncertain information into one range;
    S3, combining the uncertainty of the boundary with a loss function and forming a three-way loss function; calculating, by the loss function, a cross entropy loss between a retinal blood vessel prediction boundary map $I_{predict}$ and a retinal blood vessel manual segmentation gold standard map $I_{true}$, a cross entropy loss between the upper bound map $I_{dilate}$ of the uncertain boundary of the retinal blood vessel and the lower bound map $I_{erose}$ of the uncertain boundary of the retinal blood vessel; and generating, by a weighted fusion mode, an eventual loss, wherein a formula for calculating the eventual loss is as follows:

$$\text{Loss} = l_1 + \alpha \times l_2 + (1 - \alpha) \times l_3 \quad (1)$$

wherein $l_1$ denotes the cross entropy loss between the retinal blood vessel prediction image $I_{predict}$ and the retinal blood vessel manual segmentation gold standard map $I_{true}$, and $l_1$ is calculated as shown in Formula (2); $l_2$ denotes a cross entropy loss between the retinal blood vessel prediction image $I_{predict}$ and the lower bound map $I_{dilate}$ of the uncertain boundary of the retinal blood vessel constructed based on the erosion operator, $l_2$ is calculated as shown in Formula (3); $l_3$ denotes a cross entropy loss between the retinal blood vessel prediction image $I_{predict}$ and the upper bound map $I_{erose}$ of the uncertain boundary of the retinal blood vessel constructed based on the dilation operator, $l_2$ is calculated as shown in Formula (4); $\alpha$ and $1-\alpha$ are hyperparameters, $\alpha$ denotes a loss weight between the retinal blood vessel prediction image $I_{predict}$ and the lower bound map $I_{erose}$ of the uncertain boundary of the retinal blood vessel, and $1-\alpha$ denotes a loss weight between the retinal blood vessel prediction image $I_{predict}$ and the upper bound map $I_{dilate}$ of the uncertain boundary of the retinal blood vessel;

$$l_1 = -\sum_{i=1}^{n} I_{true} \log(I_{predict}) \quad (2)$$

$$l_2 = -\sum_{i=1}^{n} I_{erose} \log(I_{predict}) \qquad (3)$$

$$l_3 = -\sum_{i=1}^{n} I_{dilate} \log(I_{predict}) \qquad (4)$$

wherein n denotes a number of categories contained in the images; and training by adopting a stochastic gradient descent algorithm, network parameters by utilizing a total loss of the three-way loss function; and S4, implementing, by utilizing a Django framework in Python, an auxiliary diagnosis application system for intelligently segmenting the retinal blood vessel, wherein the application system includes a fundus data acquisition, an intelligent accurate segmentation for a retinal blood vessel and an auxiliary diagnosis for the retinal blood vessel, the fundus data acquisition is collecting basic information on a patient as well as left and right eye images of the patient captured by medical equipment, the intelligent accurate segmentation for the retinal blood vessel is segmenting the blood vessels in the captured left and right eye images of the patient by utilizing a U-Net model based on the three-way loss function (TWD-UNet), and uploading segmentation results to a remote diagnostic module; the auxiliary diagnosis is the doctor analyzes a patient's condition and provides diagnostic advice according to the basic information on the patient, color left and right eye images captured by a fundus camera and a corresponding segmented image of the retinal blood vessel to generate a downloadable and printable electronic diagnosis report wherein the downloadable and printable electronic diagnosis report provides personalized medical services for the patient.

2. The three-way U-Net method for accurately segmenting the uncertain boundary of the retinal blood vessel according to claim 1, wherein in specific steps of the Step S2 are as follows:

S2.1, eroding, by utilizing Formula (5), a M×M×3 retinal blood vessel image I to eliminate tiny targets in the retinal blood vessel image, wherein Formula (5) is as follows:

$$I \ominus D = \{x, y \mid (D)_{xy} \subseteq I\} \qquad (5)$$

wherein $$D = \begin{bmatrix} 1 & 1 & 1 \\ 1 & 1 & 1 \\ 1 & 1 & 1 \end{bmatrix}$$

denotes a structure element, a center is taken as an anchor point in the structure element D, the structure element D is slid on the retinal blood vessel image I with the anchor point O as the center, an entire image is traversed, a value for a pixel point at a position in the image where the anchor point is passed is set as a minimum value for a pixel point in the image corresponding to the structure element;

S2.2, dilating, by utilizing Formula (6), the M×M×3 retinal blood vessel image I to enlarge an area of a target region; and S2.3, fusing, by the dilation of the image, the target regions to infill small particle noises in the target regions, since a distance between the target regions is close, a formula for the dilation is as follows:

$$I \oplus E = \{x, y \mid (E)_{xy} \cap I \neq \emptyset\} \qquad (6)$$

wherein $$E = \begin{bmatrix} 1 & 1 & 1 \\ 1 & 1 & 1 \\ 1 & 1 & 1 \end{bmatrix}$$

denotes a structure element, a center is taken as an anchor point in the structure element E, the structure element E is slid on the retinal blood vessel image I with the anchor point O as the center, the entire image is traversed to determine whether an intersection of pixel values in the structure element region and in the corresponding image area is empty, if the intersection is an empty set, an image position corresponding to the anchor point of the structure element is set to 0, else, the image position corresponding to the anchor point of the structure element is set to 1.

* * * * *